US006728589B1

(12) United States Patent
Delache et al.

(10) Patent No.: US 6,728,589 B1
(45) Date of Patent: Apr. 27, 2004

(54) CUSTOMIZED RESPIRATORY MASK AND METHOD OF MANUFACTURING SAME

(75) Inventors: Alain J. Delache, Nice (FR); Gary Hansen, Eden Prairie, MN (US); Bruce Bowman, Eden Prairie, MN (US)

(73) Assignee: Mallinckrodt Inc., St. Louis, MO (US)

( * ) Notice: Subject to any disclaimer, the term of this patent is extended or adjusted under 35 U.S.C. 154(b) by 495 days.

(21) Appl. No.: 09/692,173

(22) Filed: Oct. 20, 2000

(51) Int. Cl.[7] .......................... G06F 19/00; A61M 16/06
(52) U.S. Cl. .................... 700/117; 700/163; 700/195; 128/206.21
(58) Field of Search ............................. 700/60, 117, 97, 700/98, 118, 160, 161, 163, 195; 2/173, 206; 128/205.25–207.13; 409/80; 131/329; 250/554.22, 554.23; 264/222; 382/111; 600/587; 356/603

(56) References Cited

U.S. PATENT DOCUMENTS

| | | | |
|---|---|---|---|
| 4,123,148 A | 10/1978 | Laird | 350/293 |
| 4,321,551 A | 3/1982 | Bleil et al. | 330/4.3 |
| 4,658,811 A | 4/1987 | Beaird | 128/163 |
| 4,907,584 A | 3/1990 | McGinnis | 128/206.24 |
| 4,934,386 A * | 6/1990 | Walker et al. | 131/329 |
| 5,056,162 A | 10/1991 | Tirums | 2/412 |
| 5,283,694 A | 2/1994 | Frady | 359/719 |
| 5,357,439 A | 10/1994 | Matsuzaki et al. | 364/468 |
| 5,454,369 A | 10/1995 | Müller et al. | 128/206.24 |
| 5,459,329 A | 10/1995 | Sinclair | 250/559.29 |
| 5,492,440 A * | 2/1996 | Spaan et al. | 409/80 |
| 5,559,334 A | 9/1996 | Gupta et al. | 250/360.1 |
| 5,587,912 A | 12/1996 | Andersson et al. | 364/468.04 |
| 5,629,808 A | 5/1997 | Powell | 359/719 |
| 5,647,357 A | 7/1997 | Barnett et al. | 128/206.24 |
| 5,659,478 A | 8/1997 | Pennisi et al. | 364/468.01 |
| 5,721,416 A | 2/1998 | Burghardt et al. | 219/121.73 |
| 5,753,931 A * | 5/1998 | Borchers et al. | 250/559.22 |
| 6,069,748 A | 5/2000 | Bietry | 359/719 |

FOREIGN PATENT DOCUMENTS

WO    WO 00/59567    * 10/2000

OTHER PUBLICATIONS

Grimson, W. et al. "Image–Guided Surgery", *Scientific American*, Jun. 1999, pp. 63–69.
Plassmann, P. et al., "Methods of Measuring Wound Size A Comparative Study", *Wounds*, Mar./Apr. 1994, vol. 6, No. 2, pp. 54–61.
Frantz, R. et al., "Stereophotography and Computerized Image Analysis: A Three–Dimensional Method of Measuring Wound Healing", *Wounds*, Mar./Apr. 1992, vol. 4, No. 2, pp. 58–64.
Goldstein, R. et al., "Influence of Noninvasive Positive Pressure Ventilation on Inspiratory Muscles", *Chest*, vol. 99, No. 2, Feb. 1991, 6 pages.
McDermott, I. et al., "Custom–Fabricated Interfaces for Intermittent Positive Pressure Ventilation", *Int. J. Prosthodontics*, vol. 2, No. 3, 1989, 5 pages.

(List continued on next page.)

*Primary Examiner*—Leo Picard
*Assistant Examiner*—Steven R. Garland
(74) *Attorney, Agent, or Firm*—Rothwell, Figg, Ernst & Manbeck, PC

(57) ABSTRACT

An apparatus and method for making a customized respiratory mask without contacting a facial area of the subject is provided according to the invention. The apparatus includes an image capturing device for capturing an image of the facial area as a three-dimensional representation without contacting a facial area of the subject, a cutting machine, and at least one computer capable of receiving the three-dimensional representation of the image and storing the three-dimensional representation in an associated memory, and which is further capable of converting the three-dimensional representation into a set of commands and controlling the cutting machine using the set of commands to cut a mask blank to form the customized respiratory mask.

29 Claims, 10 Drawing Sheets

OTHER PUBLICATIONS

Sullivan, C.E. et al., "Home Treatment of Obstructive Sleep Apnoea with Continuous Positive Airway Pressure Applied Through A Nose–Mask", *Bull Eur. Physiopathol. Respir.*, vol. 20, 1984, 3 pages.

Carroll, N. et al., "Intermittent Positive Pressure Ventilation by Nasal Mask: Technique and Applications", *Intensive Care Med*, vol. 14, 1998, pp. 115–117.

Klefbeck, B. et al., "A New Nasal Mask for Nocturnal Home Ventilation in Chronic Neuromuscular Disorders", *Scand J Rehab*, vol. 25, 1993, pp. 7–9.

Remmers, J. et al., "Nasal Airway Positive Pressure in Patients with Occlusive Sleep Apnea," *Am Rev Respir Dis*, vol. 130, 1984, pp. 1152–1155.

Gacouin, A et al., "Long–Term Nasal Intermittent Positive Pressure Ventilation (NIPPV) in Sixteen Consecutive Patients with Brochiectasis: A Restrospective Study", *Eur Respir J.*, vol. 9, 1996, pp. 1246–1250.

Cox, J. et al., "Individual Nasal Masks and Intranasal Tubes", *Anaesthesia*, vol. 29, 1974, pp. 597–600.

Hall, G, "USAF Custom Fit Oxygen Mask Program", *Aerospace Medicine*, Jun. 1972, pp. 679–680.

Suganuma, M et al., "Three–Dimensional Shape Analysis By Use of A Projected Grating Image", *Optical Engineering*, vol. 30, No. 10, Oct. 1991, pp. 1529–1532.

Jalkio, J. et al, "Three Dimensional Using Multistripe Structured Light", *Optical Engineering*, vol. 24, No. 6, 1985, pp. 966–974.

Alexander, B. et al., "3–D Shape Measurement by Active Triangulation Using an Array of Coded Light Stripes", *SPIE*, vol. 850, 1987, pp. 199–209.

Krieger, J. et al., "Essai Multicentrique D'un Dispositif De Traitement Des Apnées Obstructives Du Sommeil Par La Pression Positive Continue", *Bull. Eur. Physiophathol. Respir.*, vol. 22, 1986, 3 pages.

Mersch, S. et al., "Projecting and Using Multiple Lines of Laser Light", *SPIE*, vol. 850, 1987, 14 pages (cover, pp. 6–13 & 6–15 to 6–26).

Compére, J. et al., "Utilisation du'un Masque Personnalisé de Ventilation Par Voie Nasale Chez Les Malades Atteints de Myophathie de Duchenne", vol. 91, No. 4, 1990, pp. 313–318, Rev. Stomatol. Chir. Maxillofac.

Wright Patterson Air Force Base Webpage, "AAOM: Development of Oxygen Mask Using Surface Scanning and Rapid Prototyping", http://cfhnetra.al.wpafb.af.mil/cardlab/oxygen_masks.html, 2 pages, 1998.

Wright Patterson Air Force Base Webpage, "Surface Scanning to Quantify the Wound Healing Process", http://cfhnetra.al.wpafb.af.mil/cardlab/wound_healing.html, 4 pages, 1998.

Wright Patterson Air Force Base Webpage, "Surface Scanning and Prototyping Applied to Improve the Fit of Total Contact Burn Masks", http://cfhnetra.al.wpafb.af.mil/cardlab/burn_masks.html, 2 pages, 1998.

Wright Patterson Air Force Base Webpage, "Feature Envelopes," http://cfhnetra.al.wpafb.af.mil/cardlab/feature_env.html, 3 pages, 1998.

Sident Dental Systems Webpage, "Siemens Cerec2", www.sident.co.uk/cerec2.html, 2 pages, 1998.

MetaCreations brochure, "MetaCreations Real Time Geometry Lab Scanning Technology," 1 page, 1998.

Patterson Dental Supply brochure, "Introducing CEREC2 from SIEMENS," 1 page, 1998 or earlier.

* cited by examiner

CUSTOMIZED RESPIRATORY MASK AND METHOD OF MANUFACTURING SAME

BACKGROUND OF THE INVENTION

1. Field of the Invention

The present invention relates generally to the field of respiratory masks.

2. Description of the Background Art

A respiratory mask is a device used to deliver a gas or gases to a person. In its simplest form, the respiratory mask includes a shell, an attaching means, and a gas supply hose. The respiratory mask may be used to deliver any variety of gases, including air or oxygen, and a variety of medicines or treatments.

The shell is fitted over a nose portion of the face of the person in order to supply a gas to a respiratory system of the person. Preferably, the shell does not allow a supplied gas to escape. A strap or other attaching means may be fitted over the head of the person. Constant pressure gas is therefore delivered, with the mask also including an exhalation hole whereby a constant pressure is maintained in the mask. This is referred to as a continuous positive airway pressure (CPAP) mask. The exhalation hole allows the patient to exhale without a pressure buildup in the mask.

Related art respiratory masks are commonly made in several standard sizes. They are commonly fitted and chosen by trying on several standard mask sizes and shapes. The potential wearer may find a comfortable fit if he or she happens to be close to a standard size and shape. The related art mask, however, as a matter of economy is designed to only accommodate standard facial types.

The standard respiratory mask of the related art has several drawbacks. First, the related art respiratory mask shell may form a poor seal with the face of the person, since it only conforms to standard sizes and shapes. Leakage of the supplied gas may be critical in applications where a specific amount of gas must be measured and delivered. Second, the related art respiratory mask shell may not accommodate differences in the shape or size of features, causing a painful or uncomfortable fit. This may include undesirable pressure points. Third, a related art respiratory mask respiratory mask shell, due to a poor fit, may not stay in place, and may shift or move.

Related art masks have attempted to solve these drawbacks by creating customized masks made exclusively for a particular subject. This involves taking an impression of the subject's face. The impression may be used to create a mold from which a custom mask may be made. However, creating an impression in some sort of moldable material involves pressing the material against the subject's face. Aside from problems in breathing, problems arise with comfort, convenience, skin irritation, and irritating or noxious vapors. In addition, such a material must be flexible and pliant, and this may allow the impression to become distorted if proper care is not taken during the process.

Therefore, there remains a need in the art for an improved respiratory mask.

SUMMARY OF THE INVENTION

An apparatus for making a customized respiratory mask without contacting a facial area of the subject is provided according to a first aspect of the invention. The apparatus comprises an image capturing means for capturing an image of the facial area as a three-dimensional representation without contacting a facial area of the subject, a cutting machine, and at least one computer capable of receiving the three-dimensional representation of the image and storing the three-dimensional representation in an associated memory, and is further capable of converting the three-dimensional representation into a set of commands and controlling the cutting machine using the set of commands to cut a mask blank to form the customized respiratory mask.

A computer-implemented method for making a customized respiratory mask for a subject without contacting a facial area of said subject is provided according to a second aspect of the invention. The method comprises the steps of capturing an image of the facial area without contacting a facial area of the subject, converting the image into a three-dimensional representation of the facial area, and controlling a cutting machine to cut a respiratory mask blank part to substantially copy the three-dimensional representation, wherein a computer controls the capturing, converting, and controlling steps to create the customized respiratory mask to substantially conform to the facial area of the subject.

The above and other features and advantages of the present invention will be further understood from the following description of the preferred embodiment thereof, taken in conjunction with the accompanying drawings.

DETAILED DESCRIPTION OF THE PREFERRED EMBODIMENTS

Figure 1:
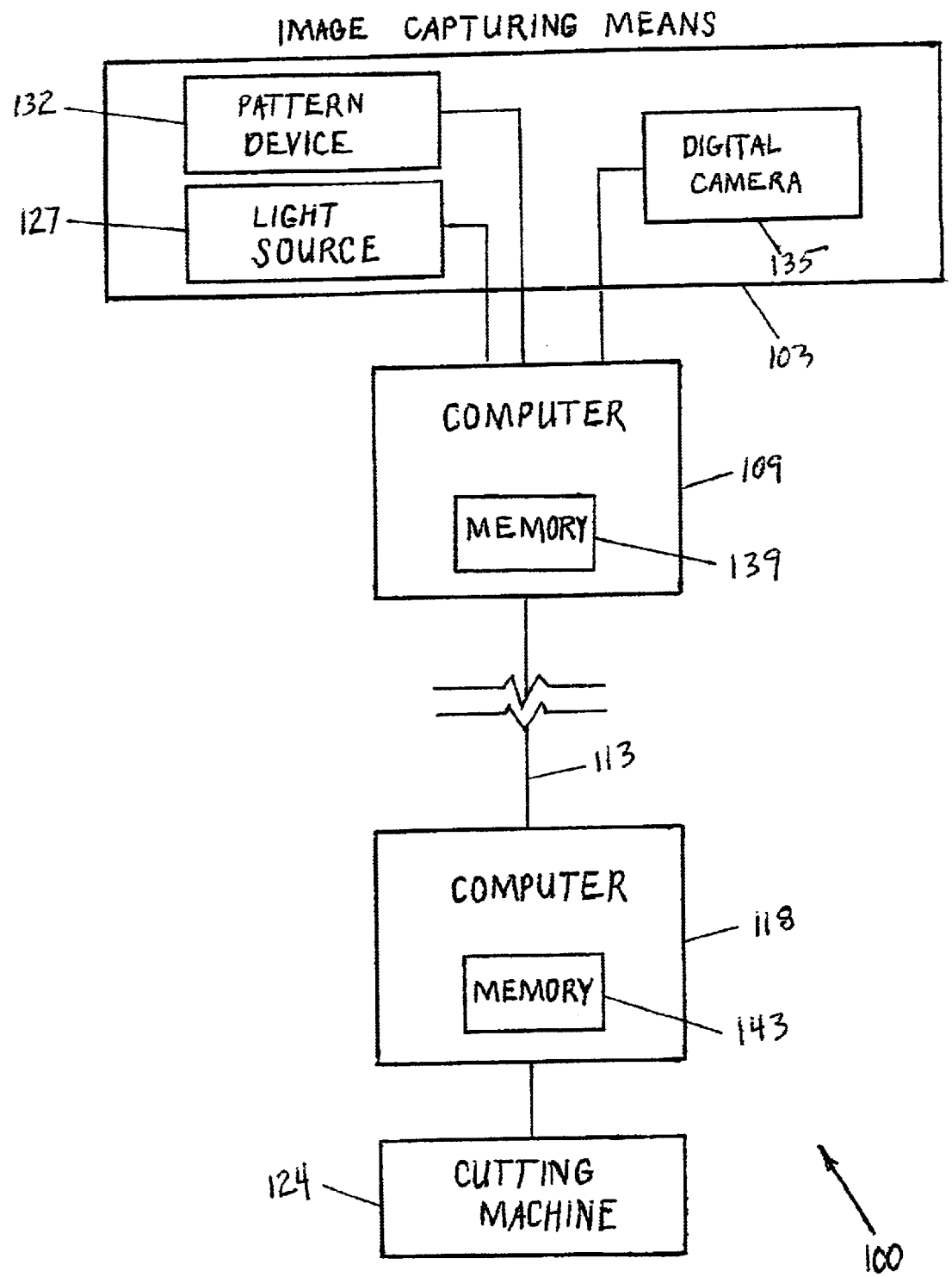
FIG. 1 shows an apparatus for making a customized respiratory mask for a subject without contacting a facial area of the subject.

FIG. 1 shows an apparatus 100 for making a customized respiratory mask for a subject without contacting a facial area of the subject. The apparatus 100 includes an imaging means 103, a first computer 109 having a memory 139, an optional communications link 113, an optional second computer 118 having a memory 143, and a cutting machine 124.

The image capturing means 103 may further include a light source 127, a pattern device 132, and a digital camera 135.

The image capturing means 103 captures an image of a facial area of a subject. In the preferred embodiment, the image capturing means 103 captures the image by illuminating the facial area through use of the light source 127 and the pattern device 132, and captures the illuminated facial area in a digital data format through the use of the digital camera 135. The image therefore contains the facial area as illuminated by a predetermined pattern of light. The purpose of the pattern of light is to enable the detection of the contours and elevations of the facial area of the subject, with the detection done automatically by a computer. In alternative embodiments, the image capturing means 103 may be a stereo photography camera or a contour photography camera.

The light source 127 in the preferred embodiment is a laser diode that emits laser light. Laser light is preferred because the light is coherent and does not need to be focused, and it is emitted in a small beam.

The pattern device 132 creates a predetermined light pattern to be projected onto the facial area of the subject. The pattern device 132 may be formed of any combination of lenses, beam splitters, mirrors, or shadow grids. In the preferred embodiment, the light pattern projected onto the facial area of the subject is nineteen parallel, substantially horizontal lines. The horizontal lines may be generated by a number of possible methods known in the art. A preferred embodiment uses a laser diode with appropriate optics to generate a plurality of lines upon the field-of-view of the camera, for example using methods described in U.S. Pat. Nos. 4,123,148, 4,321,551, 5,283,694, 5,629,808, 5,721,416 and 6,069,748. Another less preferred embodiment uses non-coherent (i.e., "white") light projected through a patterned mask. The former methods are preferable because the resulting lines have greater contrast and uniformity of brightness.

The digital camera 135 may be any type of digital camera. In the preferred embodiment, the digital camera 135 is a Kodak model DC120 digital camera. The digital camera 135 captures an image of the illuminated facial area in a digital image data format. The digital image data can be easily stored, transferred, or manipulated.

The first computer 109 may be any type of general purpose or application specific computer. The memory 139 may be any type of computer memory, including, for example, random access memory (RAM), read-only memory (ROM), magnetic tape, card, or disc, or optical memory. The first computer 109 may optionally control the light source 127, the pattern device 132, and the digital camera 135 as part of the image capturing process. The first computer 109 may receive the image data from the digital camera 135 and may store it. The first computer 109 is optional, and is not needed if the image capturing means 103 is directly connected to the second computer 118. The need for the first computer 103 is only contemplated if the image capturing means 103 is remotely located, wherein an image of the facial area of the subject may be captured at one location, stored in the first computer 109 (in the memory 139), and then transferred to a second location for the actual forming of the customized mask. In this manner, mask measuring stations may be distributed throughout an area and linked to a central manufacturing facility. A subject may use an image capturing means 103 to measure his or her face, with the digital image data being transmitted to the remote manufacturing facility. The customized mask is formed at the remote manufacturing facility. Delivery of the final product may be through any type of mail or package delivery.

The communications link 113 may be any type of digital electronic communications link, such as a telephone line accessed by a modem (not shown), or a computer network, such as, for example, a local area network (LAN), a wide area network (WAN), or the Internet. As in the first computer 109, the communications link 113 is optional, and may be included if the image capturing means 103 is remote from and not directly connected to the second computer 118.

The second computer 118 may be any type of general purpose or application specific computer. The memory 143 may be any type of computer memory, including, for example, random access memory (RAM), read-only memory (ROM), magnetic tape, card, or disc, or optical memory. The second computer 118 may receive and process image data generated by the image capturing means 103. Alternatively, when the first computer 109 is included in the apparatus 100, the first computer 109 may process the image data. The image processing is discussed below in conjunction with FIG. 3. The second computer 118 converts image data into a three dimensional representation that controls a depth of cut in the cutting of a blank mask shell in order to form a customized respiratory mask.

The cutting machine 124 may be any type of general cutting machine that is capable of being computer controlled, such as a computer numerical control (CNC) cutting machine. The cutting machine 124 is controlled by the second computer 118 to follow the contours of the three-dimensional representation of the image. The major components of the cutting machine 124 are discussed below in conjunction with FIG. 7.

Figure 2:
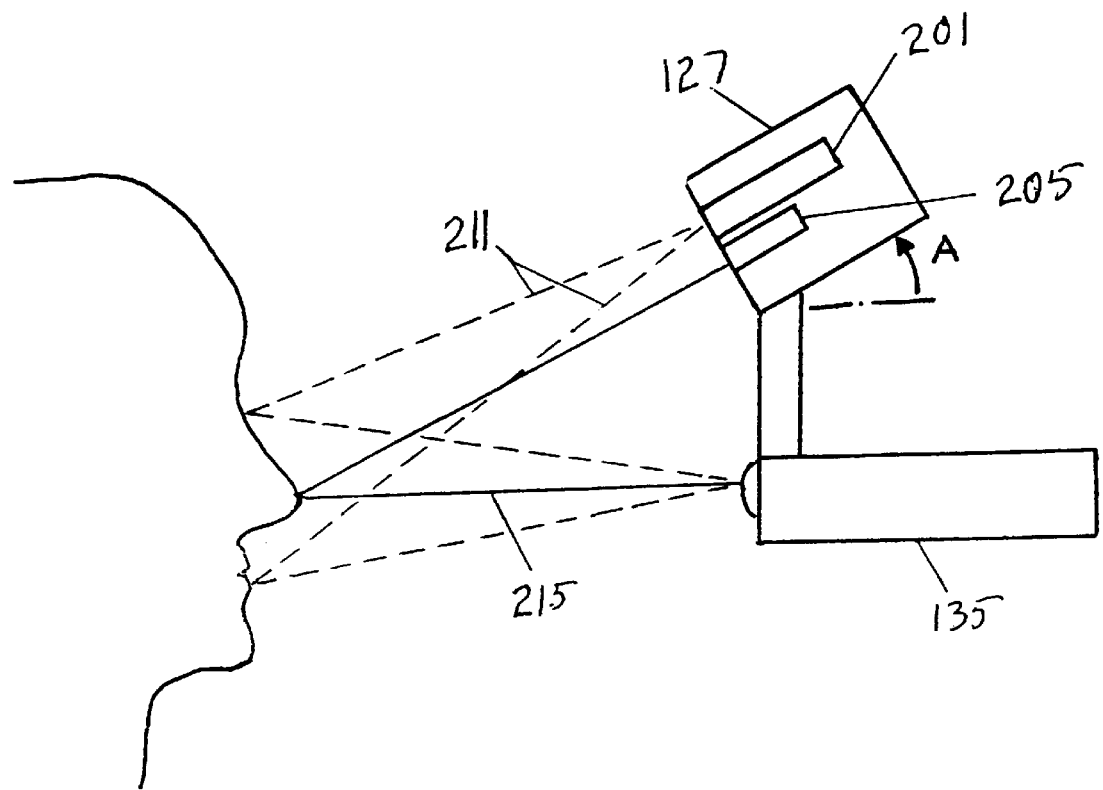
FIG. 2 shows a side view of one embodiment of the image capturing means.

FIG. 2 shows a side view of one embodiment of the image capturing means 103, showing placement of components in relation to the facial area of the subject. The figure shows the digital camera 135, having the light source 127 attached thereto. The light source further includes a laser diode 201 and an alignment beam generator 205. The alignment beam generator 205 generates an alignment beam 215 that is used to position the system substantially in alignment with the subject's facial features. The laser diode is capable of generating a plurality of lines of light, such as lines 211. The lines 211 illuminate the facial area in a predetermined pattern. In the preferred embodiment, the pattern includes nineteen parallel, substantially horizontal lines. As can be seen in the figure, the light source 127 is positioned in front of and at an angle A above the facial area of the subject. The angle A in the preferred embodiment is about thirty degrees, although it is contemplated that the angle A may vary from ten to sixty degrees. It has been determined that through this arrangement, only one image is needed in order to determine the facial contours. In lesser preferred embodiments, the facial contours may be found through use of two or more images taken from the left and right sides of the face, or through use of alternate imaging methods such as a stereo photography camera or a contour photography camera.

Figure 3:
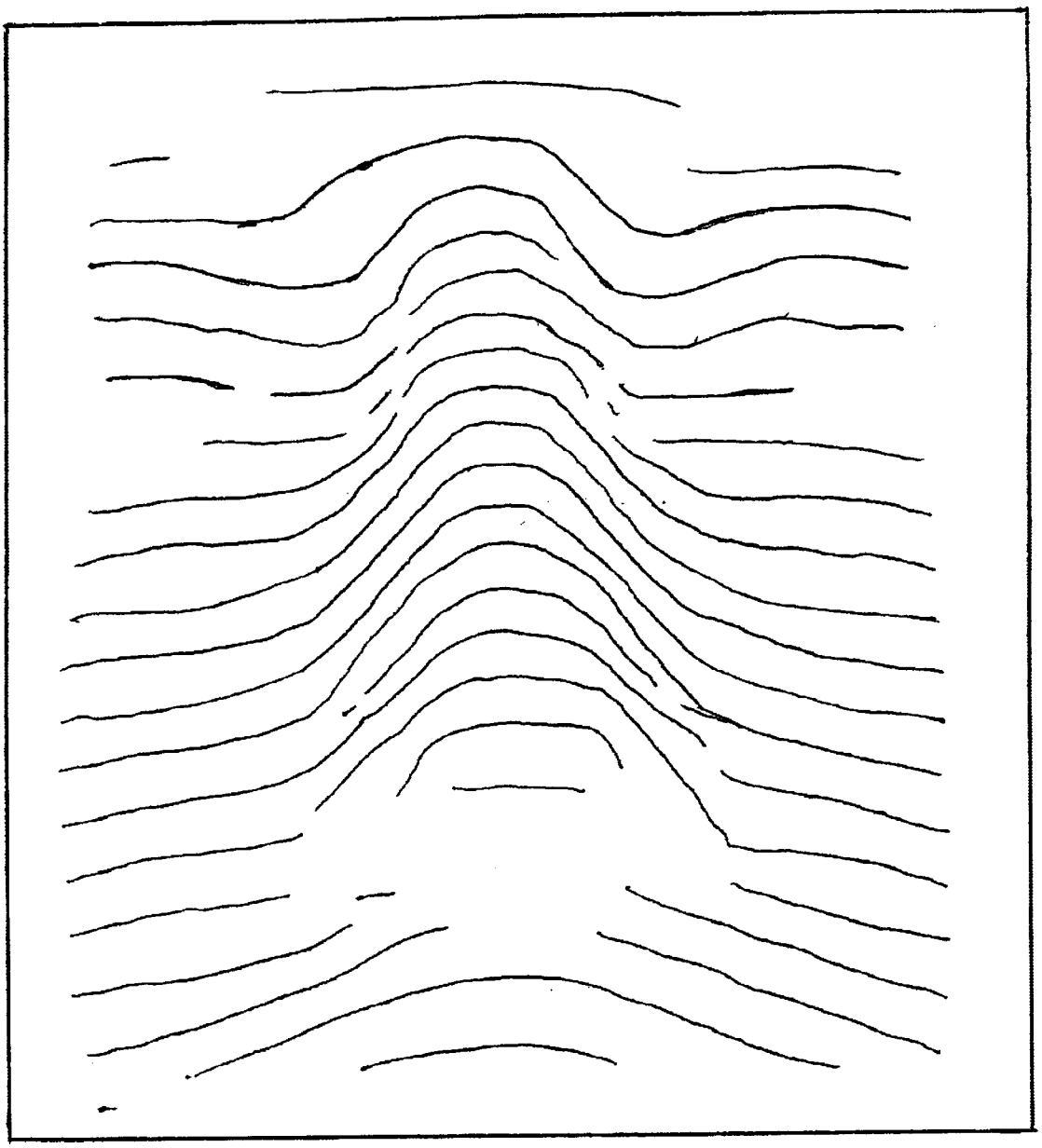
FIG. 3 shows an image captured by the preferred embodiment of the present invention.

FIG. 3 shows an image captured by the preferred embodiment of the present invention. The figure illustrates how the parallel, substantially horizontal lines of light are affected by facial contours.

Figure 4:
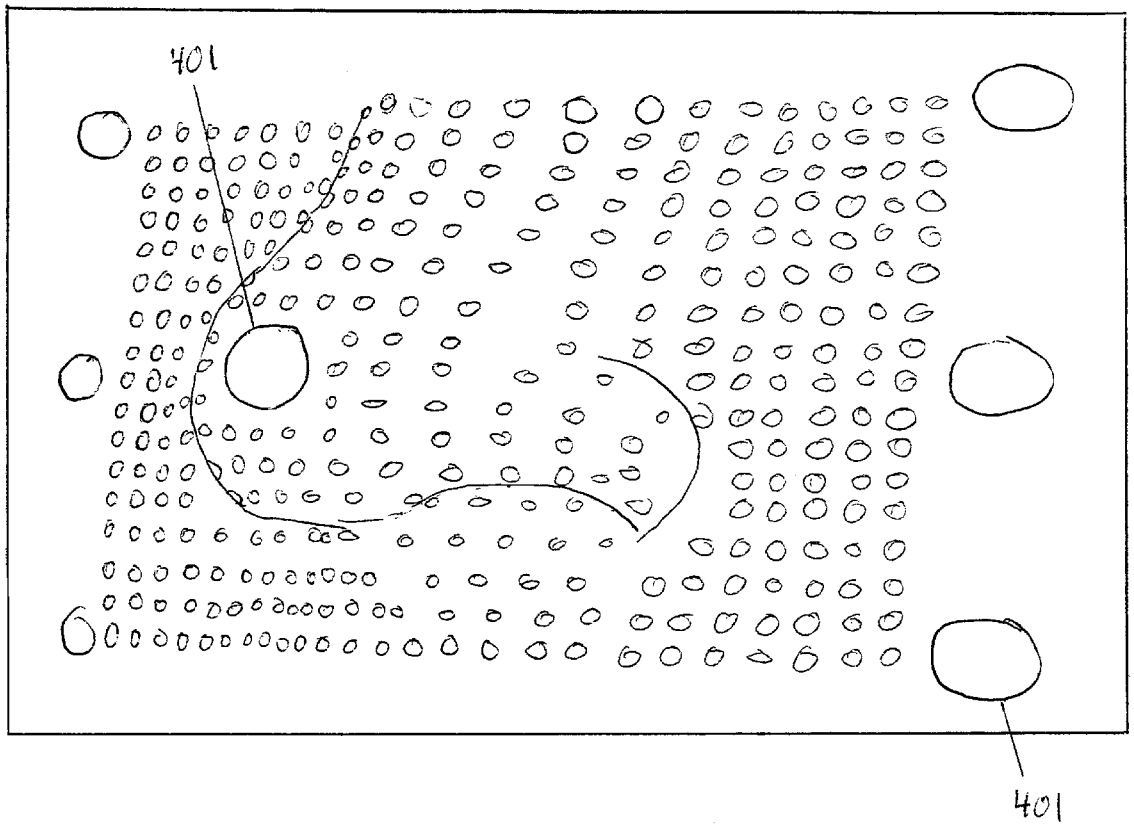
FIG. 4 shows an alternate embodiment where dots of light are used instead of lines.

FIG. 4 shows an alternate embodiment where dots of light are used instead of lines. Large dots 401 are used for alignment when converting the image into a three-dimensional representation.

Figure 5:
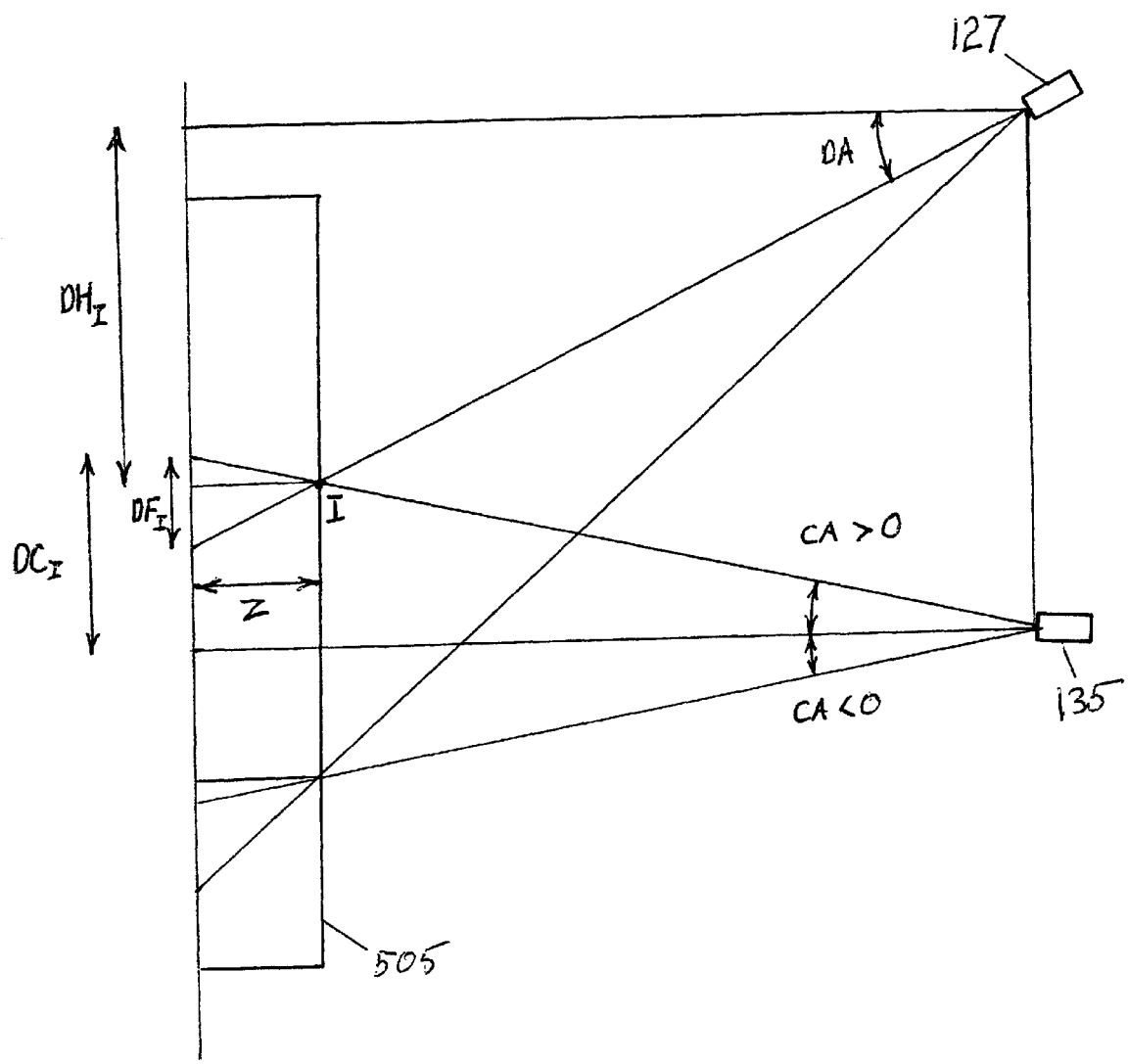
FIG. 5 shows how the image data is used to calculate height contours.

FIG. 5 shows how the image data is used to calculate height contours. The image data is preferably in digital form, and the light pattern is analyzed to determine or infer the heights of the illuminated facial contours. The light pattern, such as those shown in FIGS. 3 and 4, is analyzed by a computer and positions of the lines are extracted and stored (see discussion below accompanying FIGS. 9 and 10).

Extracted line positions are then analyzed to determine their height above a reference plane 505. The formula for determining a contour height Z at a point I is given by:

$$Z = DF_I / (\tan(DA) + \tan(CA)) \quad (1)$$

where $DF_I$ is the displacement of the image of the facial area, DA is the angle of the light source from a horizontal, and CA is the angle of a camera line from the horizontal.

Figure 6A:
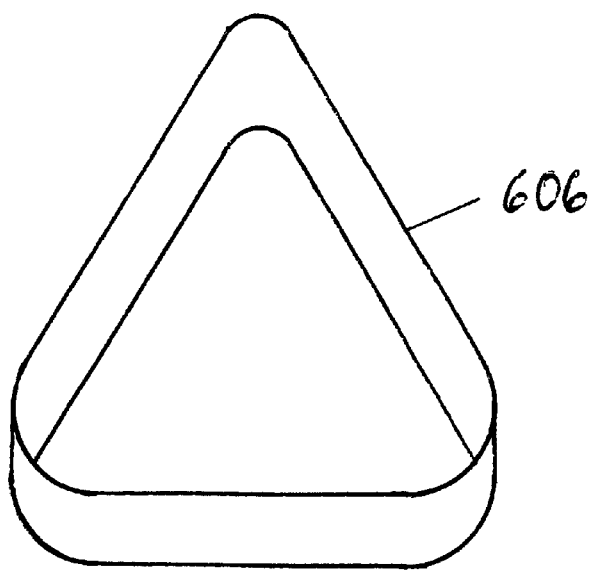
FIG. 6A shows a mask blank before the cutting operation of the present invention.

FIG. 6A shows a mask blank 606 before the cutting operation of the present invention. The mask blank 606 is shown as having a triangular, substantially mask-like shape, but alternatively the mask blank 606 may be other shapes, including square, round, or trapezoidal.

Figure 6B:
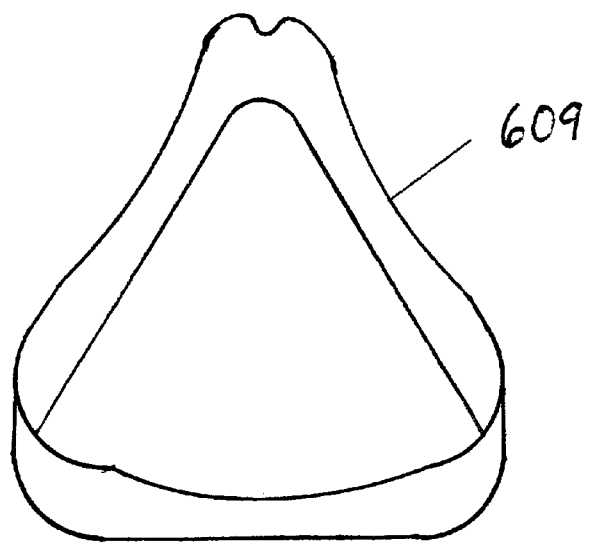
FIG. 6B shows a mask shell cut from the mask blank.

FIG. 6B shows a mask shell 609 cut from the mask blank 606. The mask shell 609 may have any shape or number of contours cut into the mask blank 606 in order to match the facial area of the subject.

Figure 7:
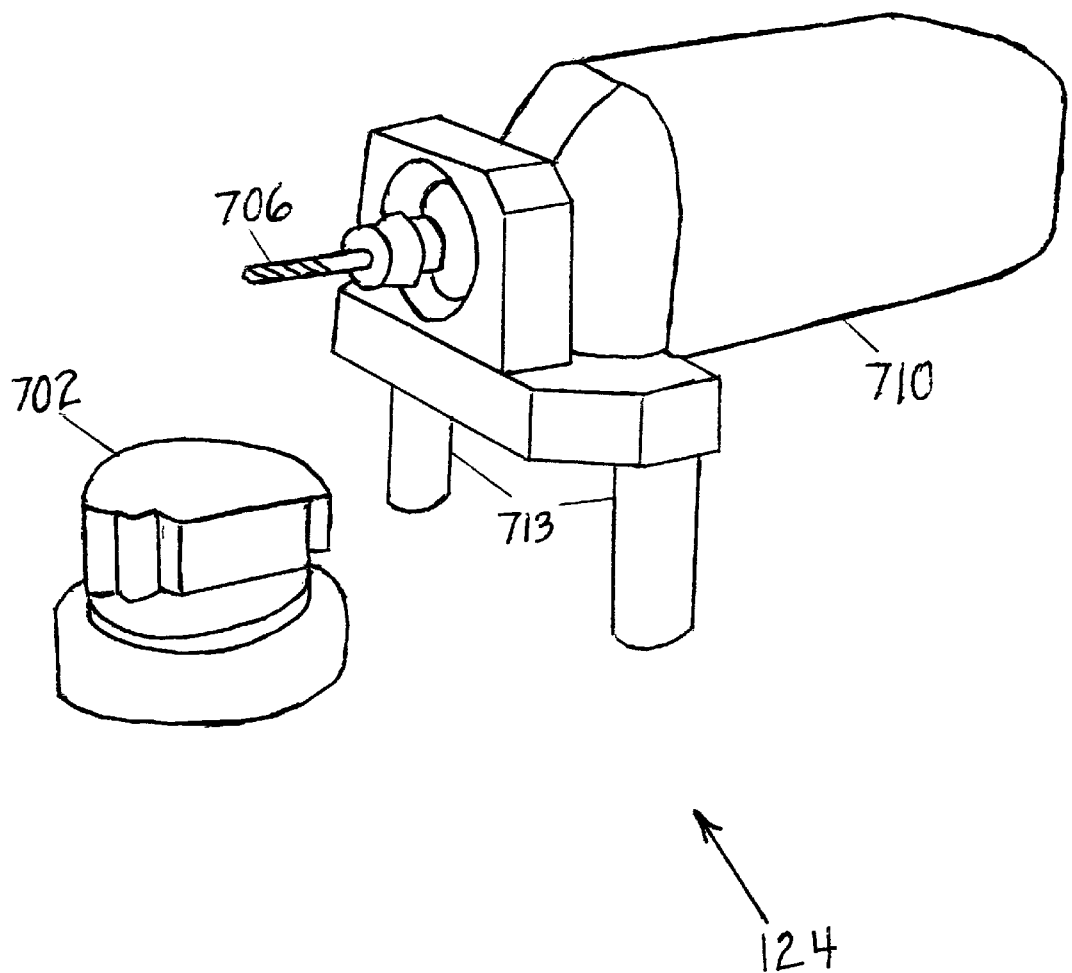
FIG. 7 shows major components of the cutting machine.

FIG. 7 shows major components of the cutting machine 124. The cutting machine 124 includes a rotating workpiece base 702, a cutting tool 706, a motor 710, and a vertical actuator 713.

In operation, the cutting tool 706 is rotated by the motor 710 in order to perform the actual cutting. The mask blank 606 is mounted on the rotating workpiece base 702. The rotating workpiece base 702 in the preferred embodiment is rotated by a stepper motor, and the second computer 118 may thereby rotate the mask blank 606 during the cutting operation. The vertical actuator 713 in the preferred embodiment is moved vertically by a stepper motor or motors, and is also controlled by the second computer 118. Alternatively, the vertical actuator 713 may be moved by pneumatic or hydraulic actuators. The mask blank 606 may therefore be cut into the measured height contours of the facial area of the subject under the control of the second computer 118, which may control the rotation of the mask blank 606 and the depth of cut being performed on the mask blank 606.

Figure 8:
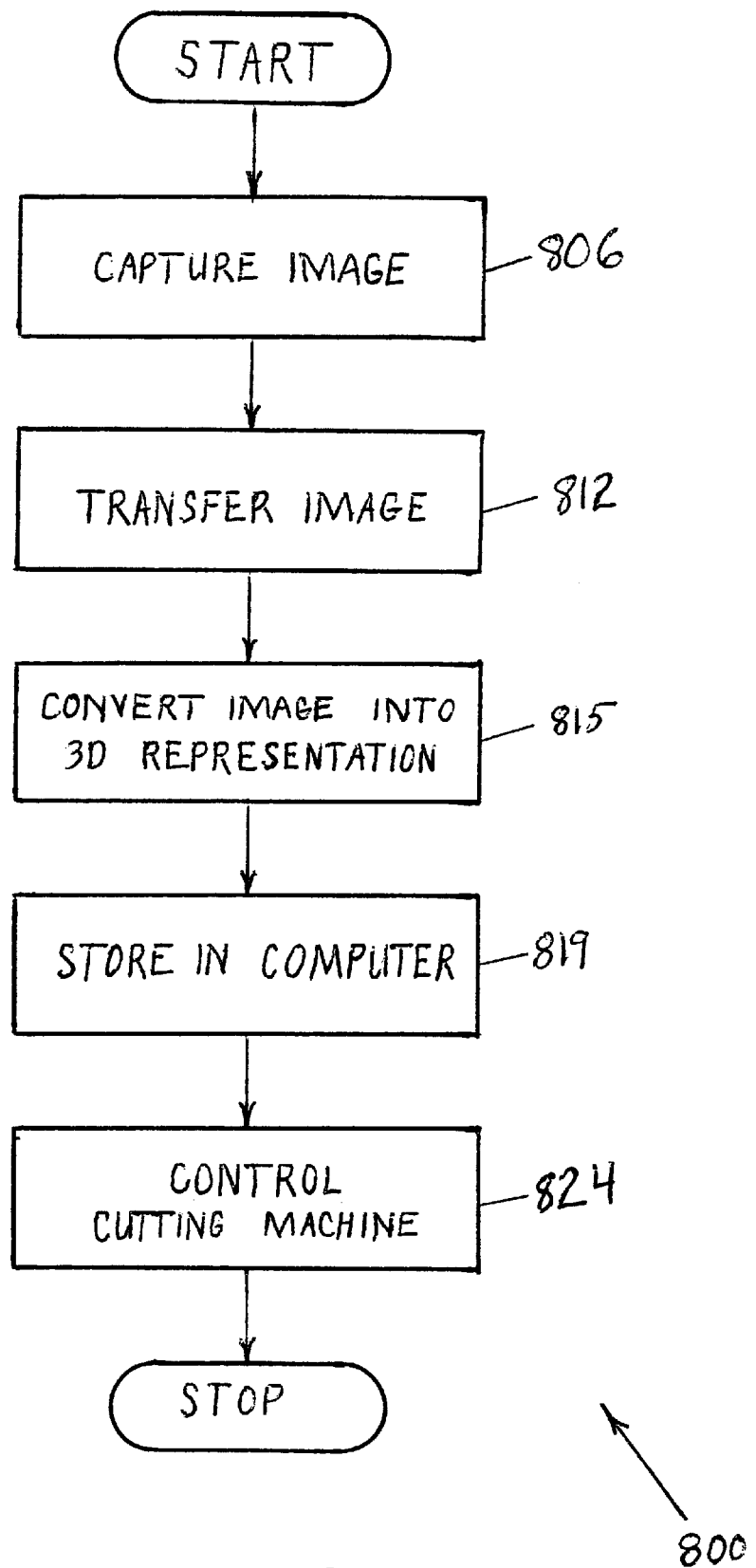
FIG. 8 shows a flowchart of the method of the present invention.

FIG. 8 shows a flowchart 800 of the method of the present invention.

In step 806, an image of the facial area of the subject is captured. The image is preferably captured in a digital format, wherein the image may subsequently be stored, transferred, or manipulated.

In optional step 812, the captured image is transferred from an image capturing means (and an associated first computer) to a remote second computer, where processing will be performed.

In step 815, the image (i.e., the image data) is converted into a three-dimensional representation of the image of the facial area. The converting step may include either pixel selection method of FIGS. 9 and 10 (discussed below), and the height determination process for each selected pixel as discussed in conjunction with FIG. 5.

In optional step 819, the three-dimensional representation is stored in the second computer 118. The image data may be stored until a time when a customized mask is manufactured. It should be understood that the storing step refers to a storing of more than transitory duration, as the data will of necessity be stored in the RAM of the second computer 118 temporarily during processing.

In step 824, the second computer 118 controls the cutting machine in order to turn the mask blank 606 into the finished mask shell 609.

Figure 9:
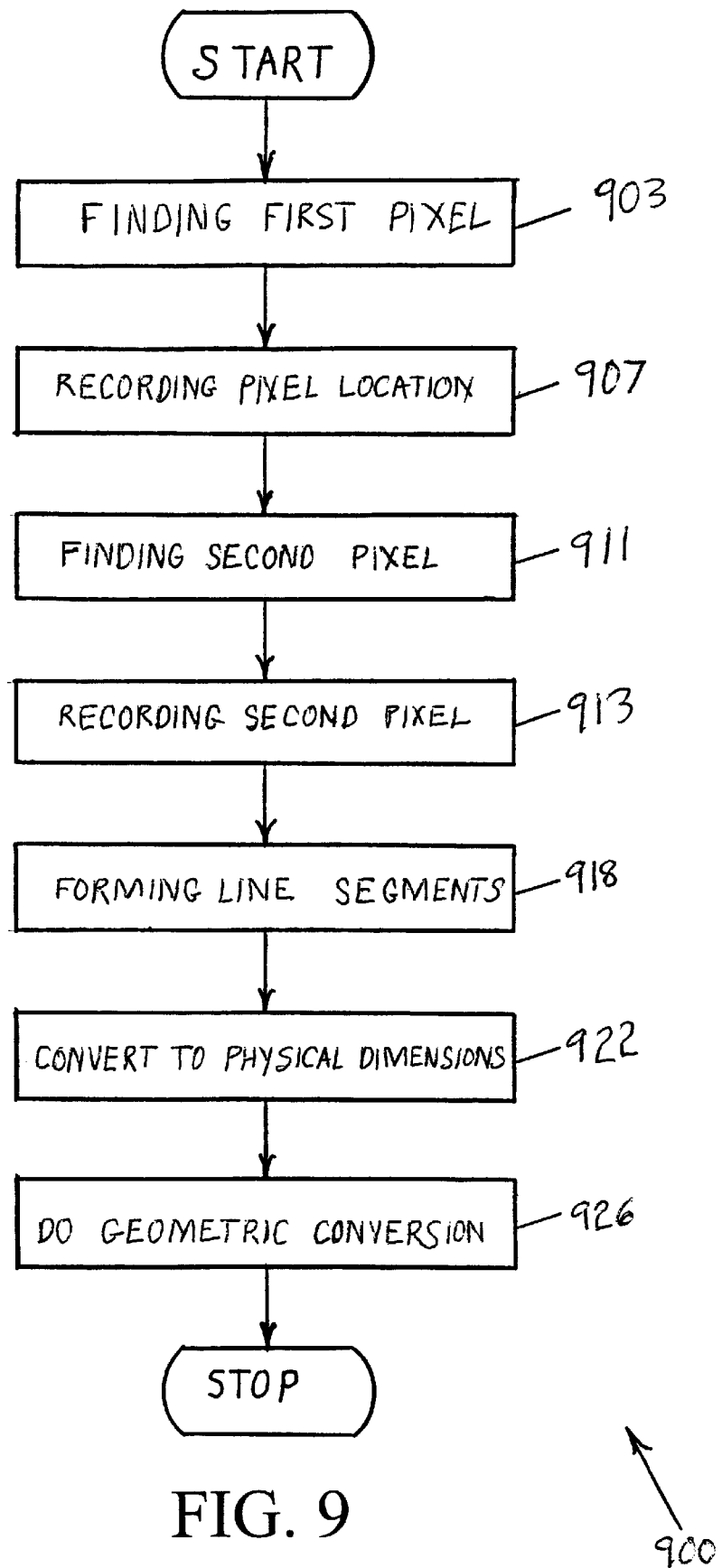
FIG. 9 shows a flowchart of a first embodiment of a pixel selection method.

FIG. 9 shows a flowchart 900 of a first embodiment of the pixel selection method.

In step 903, a first pixel of a line is selected. The pixel must exceed a predetermined brightness threshold.

In step 907, the first pixel location is recorded.

In step 911, a second pixel is selected. As in step 903, the pixel must exceed the predetermined brightness threshold. In addition, the second pixel must be contiguous to a right side of the first pixel.

In step 913, the second pixel location is recorded. The above steps of pixel selection and recordation are continued until all acceptable pixels are located. By looking at pixels contiguous to the right side of a current pixel, the method traces the lines of the light pattern of the preferred embodiment. When an end of a current horizontal line is reached, whether at an actual end or through the slope of the line, the method resumes searching for another acceptably bright pixel.

In step 918, the found pixels are used to form line segments of contiguous pixels.

In step 922, the image lines are converted into physical dimensions by applying a scaling factor. In the preferred embodiment, each pixel represents about 0.3 millimeter. The scaling factor will depend on the distance between the facial area of the subject and the digital camera 135.

In step 926, a geometric conversion is applied in order to determine the contour heights of the facial area. The height determination is performed in accordance with the formula discussed in conjunction with FIG. 5 above.

Figure 10:
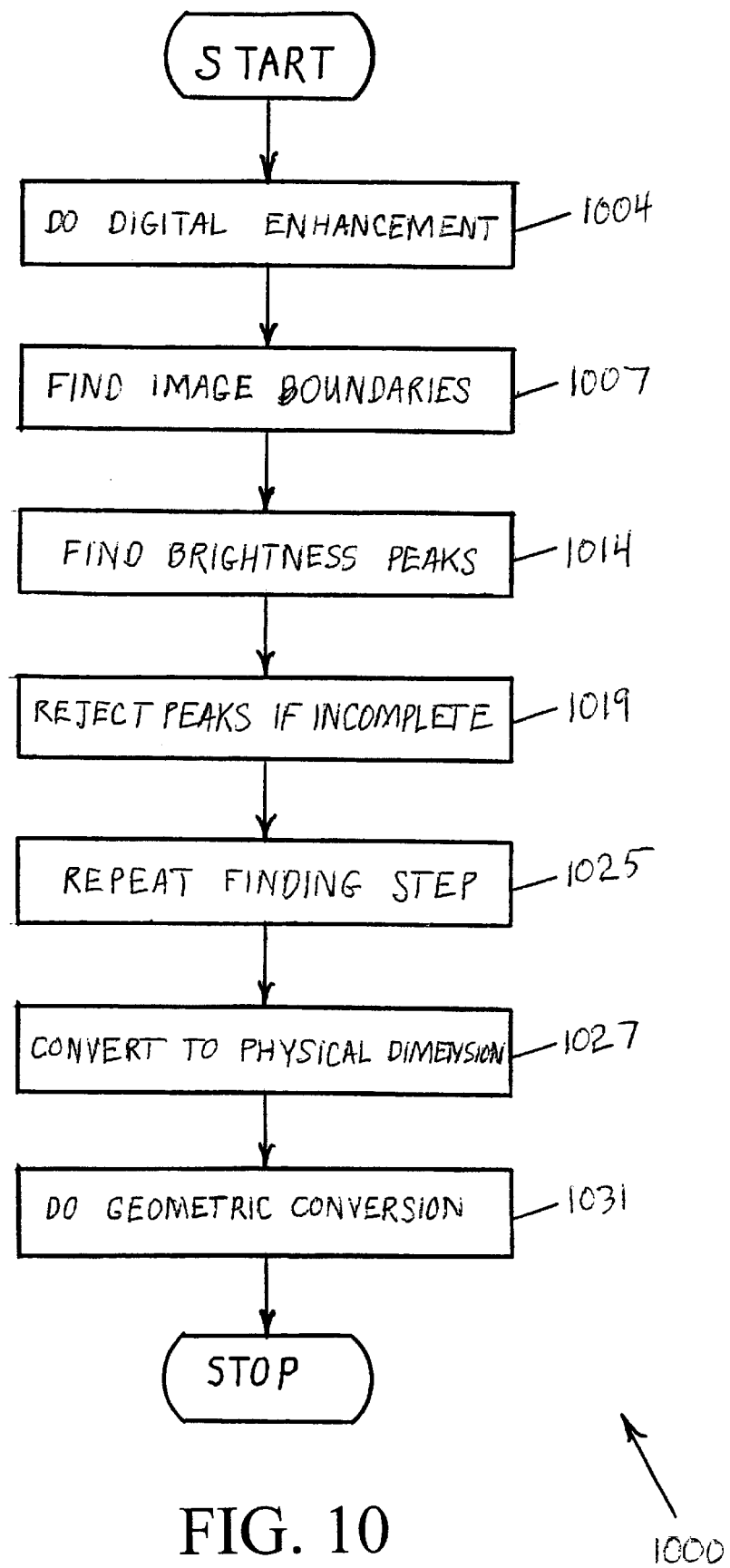
FIG. 10 shows a flowchart of a second embodiment of the pixel selection method.

FIG. 10 shows a flowchart 1000 of a second embodiment of the pixel selection method.

In step 1004, a digital enhancement is performed on the image. In the preferred embodiment, the digital enhancement method looks at a single vertical scan of pixels that cuts across the lines of the image. A maximum and minimum brightness is found, and a local scale is defined, with the scale being 255 for the maximum brightness, and 0 for the minimum. Then pixels within the image that do not exceed a predetermined brightness threshold are set to zero, while pixels that do exceed the predetermined brightness threshold are set to a value of 255. It should be understood that other enhancement methods may be used, such as standard image enhancement routines commonly used in the art.

In step 1007, the method searches inward from an edge of the image to find a maximal extent of an illumination pattern of the image. In this manner, the image boundaries are approximated.

In step 1014, all brightness peaks along a vertical line are located and recorded. The recordation includes recording the pixels associated with the brightness peaks.

In step 1019, the vertical line and the associated brightness peaks are rejected if less than a predetermined number of such peaks are found. This step ensures that areas having drop-offs or blank spots in the image do not adversely affect the final result.

In step 1025, the finding process of step 1014 is repeated a predetermined number of times. The number of vertical lines thereby inspected will control the accuracy and resolution of the method. The brightness peaks found will form the horizontal lines of the light pattern of the preferred embodiment.

In step 1027, the image lines are converted into physical dimensions by applying a scaling factor. In the preferred embodiment, each pixel represents about 0.3 millimeter.

In step 1031, a geometric conversion is applied in order to determine the contour heights of the facial area. The height determination is performed in accordance with the formula discussed in conjunction with FIG. 5 above.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. An apparatus for making a customized respiratory mask for a subject without contacting a facial area of said subject, comprising:
   an image capturing means for capturing an image of said facial area as a three-dimensional representation without contacting a facial area of said subject;
   a cutting machine; and
   at least one computer capable of receiving said three-dimensional representation of said image and storing said three-dimensional representation in an associated memory, and which is further capable of converting said three-dimensional representation into a set of commands and controlling said cutting machine using said set of commands to cut a mask blank to form said customized respiratory mask;
   wherein said computer digitally enhances said image to emphasize brightness peaks and to reduce background noise; searches inward from an edge of said image to find a maximal extent of an illumination pattern of said image; locates and records brightness peaks along a vertical line through said image, said recording including recording of pixels associated with said brightness peaks; rejects said vertical line and associated pixels if less than a predetermined number of said brightness peaks are found; repeats said locating and recording step for a predetermined number of vertical lines; converts pixel locations to physical dimensions by applying a scaling factor; and applies a geometric conversion to determine a contour height from said pixel locations.

2. The apparatus of claim 1, wherein said image capturing means further includes a stereo photography camera.

3. The apparatus of claim 1, wherein said image capturing means further includes a contour photography camera.

4. The apparatus of claim 1, wherein said image capturing means further includes:
   a light source for illuminating said facial area; and
   a digital camera for capturing an image of said facial area and converting said image into a three-dimensional representation.

5. The apparatus of claim 4, wherein said light source includes a pattern projector.

6. The apparatus of claim 4, wherein said light source is a laser diode.

7. The apparatus of claim 4, wherein said light source is positioned in front of and at an angle above said facial area of said subject.

8. The apparatus of claim 7, wherein said angle is about thirty degrees.

9. The apparatus of claim 4, wherein said light source illuminates said facial area with a plurality of spaced apart substantially horizontal lines.

10. The apparatus of claim 1, wherein said memory stores said three-dimensional representation of said image as numerical data.

11. The apparatus of claim 1, wherein said apparatus further includes a communications link between said image capturing means and said computer and said cutting machine, wherein said communications link allows said image capturing means to be remotely located from said computer and said cutting machine.

12. The apparatus of claim 1, wherein said three-dimensional representation is capable of being edited before a cutting process occurs.

13. The apparatus of claim 1, wherein said cutting machine further includes:
   a turntable upon which said mask blank is mounted for a cutting operation, a rotation of said turntable being controlled by a rotary stepper motor;
   a cutting tool; and
   a vertical actuator upon which said cutting tool is mounted, said vertical actuator being capable of being vertically positioned by a vertical stepper motor;
   wherein said at least one computer controls said rotary stepper motor and said vertical stepper motor.

14. A computer-implemented method for making a customized respiratory mask for a subject without contacting a facial area of said subject, comprising the steps of:
   capturing an image of said facial area without contacting a facial area of said subject;
   converting said image into a three-dimensional representation of said facial area; and
   controlling a cutting machine to cut a respiratory mask blank part to substantially copy said three-dimensional representation;
   wherein a computer controls said capturing, converting, and controlling steps to create said customized respiratory mask to substantially conform to said facial area of said subject;
   wherein the converting step further includes the steps of:
      digitally enhancing said image to emphasize brightness peaks and to reduce background noise;
      searching inward from an edge of said image to find a maximal extent of an illumination pattern of said image;
      locating and recording brightness peaks along a vertical line through said image, said recording including recording of pixels associated with said brightness peaks;
      rejecting said vertical line and associated pixels if less than a predetermined number of brightness peaks are found;
      repeating said locating and recording step for a predetermined number of vertical lines;
      converting pixel locations to physical dimensions by applying a scaling factor; and
      applying a geometric conversion to determine a contour height from said pixel locations.

15. The method of claim 14, wherein said capturing step includes using stereo photography to capture said image.

16. The method of claim 14, wherein said capturing step includes using contour photography to capture said image.

17. The method of claim 14, wherein the step of capturing an image of said facial area further includes the steps of:
   illuminating said facial area of said subject with a light source having a predetermined pattern; and
   capturing an image of said facial area when illuminated by said predetermined pattern.

18. The method of claim 17, wherein said illuminating step illuminates said facial area with structured light.

19. The method of claim 17, wherein said illuminating step illuminates said facial area with laser light.

20. The method of claim 17, wherein said illuminating step includes illuminating said facial area with a light source positioned in front of and at an angle above said facial area of said subject.

21. The method of claim 20, wherein said angle is about thirty degrees.

22. The method of claim 17, wherein said illuminating step further includes illuminating said facial area with a plurality of spaced apart substantially horizontal lines.

23. The method of claim 14, wherein said step of capturing an image of said facial area further includes the steps of:

converting said image into a digital representation; and storing said digital representation in said computer.

24. The method of claim 14, wherein said step of converting said image into a three-dimensional representation of said facial area further includes converting said image into numerical data.

25. The method of claim 14, wherein said three-dimensional representation is transmitted to a remote site for said cutting step to be performed.

26. The method of claim 14, further including the step of adding an edge seal gasket to said customized respiratory mask.

27. The method of claim 14, wherein the converting step further includes the steps of:

finding a first pixel that exceeds a predetermined brightness threshold;

recording a location of said first pixel;

finding a second pixel that exceeds said predetermined brightness threshold and is contiguous to a right side of said first pixel;

recording a location of said second pixel;

forming line segments of contiguous pixels when all pixels have been checked;

converting pixel locations to physical dimensions by applying a scaling factor; and applying a geometric conversion to determine a contour height from said pixel locations.

28. A computer-implemented method for making a customized respiratory mask for a subject without contacting a facial area of said subject, comprising the steps of:

capturing an image of said facial area without contacting a facial area of said subject;

converting said image into a three-dimensional representation of said facial area; and controlling a cutting machine to cut a respiratory mask blank part to substantially copy said three-dimensional representation;

wherein a computer controls said capturing, converting, and controlling steps to create said customized respiratory mask to substantially conform to said facial area of said subject;

wherein said converting step further includes finding a height of a contour feature of said image from a reference plane according to a formula height=DF/(tan(DA)+tan(CA)), where DF is a deflection of said contour feature from a reference plane position, DA is an angle of an illuminating beam from a horizontal plane, and CA is an angle of a camera line from said horizontal plane.

29. An apparatus for making a customized respiratory mask for a subject without contacting a facial area of said subject, comprising:

an image capturing means for capturing an image of said facial area as a three-dimensional representation without contacting a facial area of said subject;

a cutting machine; and at least one computer capable of receiving said three-dimensional representation of said image and storing said three-dimensional representation in an associated memory, and which is further capable of converting said three-dimensional representation into a set of commands and controlling said cutting machine using said set of commands to cut a mask blank to form said customized respiratory mask;

wherein said computer converts said image into a three-dimensional representation of said facial area by finding a height of a contour feature of said image from a reference plane according to a formula height=DF/(tan(DA)+tan(CA)), where DF is a deflection of said contour feature from a reference plane position, DA is an angle of an illuminating beam from a horizontal plane, and CA is an angle of a camera line from said horizontal plane.

* * * * *